United States Patent [19]
Fuchs

[11] Patent Number: 5,873,723
[45] Date of Patent: Feb. 23, 1999

[54] PROCESS FOR MANUFACTURE OF PRECISELY FITTING DENTAL CASTINGS AND TEST MODELS FOR CARRYING OUT THE PROCESS

[76] Inventor: Theo Fuchs, St.-Gallus-Strasse 35/1, 78086 Brigachtal, Germany

[21] Appl. No.: 946,728

[22] Filed: Oct. 8, 1997

[30] Foreign Application Priority Data

Oct. 8, 1996 [DE] Germany ............. 196 41 348.6

[51] Int. Cl.⁶ ............................................. A61C 13/00
[52] U.S. Cl. ............................................. 433/213; 433/214
[58] Field of Search ........................ 433/214, 213, 433/215, 223

[56] References Cited

U.S. PATENT DOCUMENTS

| | | | |
|---|---|---|---|
| 3,905,106 | 9/1975 | Costa et al. ............... | 433/213 |
| 4,721,466 | 1/1988 | Thalheimer ............... | 433/213 X |
| 4,758,162 | 7/1988 | Dobbs ....................... | 433/213 |
| 5,201,657 | 4/1993 | Koukos ..................... | 433/213 |

*Primary Examiner*—Nicholas D. Lucchesi
*Attorney, Agent, or Firm*—Pendorf & Cutliff

[57] ABSTRACT

For the production of form fitting dental castings an imprint or impression is made from a pre-formed test body with phantom tooth stumps using the imprint material used by the dentist. Using this imprint, the dental laboratory produces a plaster test model. On this plaster model a test casting is modeled and cast. The casting matrix used for the casting is imperically so adjusted, that the test cast object achieves an optimal form fitting precision upon the test body. Future patient castings are produced using the determined value of the casting matrix.

9 Claims, 1 Drawing Sheet

PROCESS FOR MANUFACTURE OF PRECISELY FITTING DENTAL CASTINGS AND TEST MODELS FOR CARRYING OUT THE PROCESS

BACKGROUND OF THE INVENTION

1. Field of the Invention

The invention concerns a process for manufacturing precisely fitting dental castings.

2. Description of the Related Art

In the manufacture of dental castings, such as crowns, bridges and other dental prosthesis, after preparation of the tooth stumps, the dentist produces an impression of the tooth stumps. This impression is given to a dental laboratory, where the impression is filled in with a modeling material, generally plaster. The resulting model is used by the dental technician upon which to model and cast the cast objects (castings). For this the castings are modeled out of wax on the model of the tooth stumps. The wax models are embedded in a matrix, so that after melting out of the wax a hollow shape for the pouring of the castings is formed. This process is described, for example, in DE 94 12 336 U1.

If the castings made in this manner are then seated upon the tooth stumps of the patient, fitting imperfections are frequently discovered. These fitting imperfections can have numerous causes. For example, many imprint materials are available in the market with varying chemical compositions, such as for example silicones, polyether rubbers and hydrocolloids. These various materials exhibit various shape changes, usually shrinkage, during hardening or setting. Also, the utilization of varying hardeners and varying mixture relationships influence the physical properties of the imprint material. Further, the dimensions of the cast object are influenced by the various plaster model materials used for filling in the impression or negative. Thereby variations of between approximately 0.2 and 0.06 vol.% are produced in the setting or hardening expansion of the model material. Also, the mixing relationship of water to plaster powder, and the selection of distilled water or tap water with mineral contents, influences the setting or hardening relationship in the manufacture or production of the model. The largest influence on the dimension of the cast object is the mold matrix. The conventionally available mold matrix materials exhibit an expansion of between approximately 0.5 and 3.5 vol.%, wherein these expansions can be controlled or influenced by the mixing relationship and the utilization of distilled water or special mixing fluids.

In the hitherto known procedures the dental technician attempts by exercising control over the embedding matrix to produce cast objects which have an optimal form fitting precision with respect to the plaster model produced by him. The form fitting precision to the plaster model for the above discussed reasons does not however necessarily mean a corresponding form fitting precision to the tooth stumps of the patient. Thus, as a rule, there occurs a further follow-up working of the casting by the dentist or as the case may be the dental laboratory. This is associated with a high labor expenditure for the dentist and the laboratory. The multiple follow-up grindings and fittings of the casting is also inconvenient and time consuming for the patient. Finally, the follow-up working of the casting does not always lead to an optimal occlusion, which must be compensated for by larger cement fisures, which increase the vulnerability to secondary cavities.

SUMMARY OF THE INVENTION

The invention is concerned with the objective, of making available a process and a test model, which simplify or make easier the manufacture of dental castings and which improve the form fitting precision.

Advantageous embodiments of the invention are indicated in the dependent claims.

The essential concept of the invention is comprised therein, that during the production of the casting the systematically occurring fitting errors are determined with the help of a test model and the mold matrix is so adjusted, that these systematic deviations are exactly compensated. If castings are subsequently produced for a patient, then the systematic deviations are already taken into account and compensated for, without there being a need for a fitting session with the patient.

The test model or test body, which preferably is made of steel, is provided with several, for example four, polished phantom tooth stumps. The dentist makes an impression of these phantom tooth stumps in the conventional manner, wherein he employs the casting matrix which he selects and which he conventionally employs. The test body and the imprint are given to the dental laboratory, with which he has a working relationship. In the dental laboratory this impression is cast with plaster, in order to produce a plaster test model. Herein, the plaster composition and the plaster mixture and manner of preparation are employed which the laboratory conventionally employs. On this trial model, test cast shapes are modeled of wax and cast using a casting matrix. The so-cast test-cast objects are then seated upon the test body in order to check its form fitting exactness. On the basis of the conicalness or taper of the phantom tooth stumps of conventionally approximately 6° it can easily be determined if the test casting is too broad or too narrow. The expansion of the cast matrix is then empirically modified and adjusted, until the test casting fits completely precisely upon the phantom tooth stump. The fitting exactness is then checked with a microscope. The expansion and the mixture relationship information of the casting matrix, with which the optimal form fitting exactness is obtained, are then registered in the dental laboratory and stored.

In the future work of this dentist on this patient, the values for this casting material for this dentist are used in the dental laboratory, so that all system determined dimensional changes are already optimally taken into consideration and compensated for, which result for example from the amount of casting material employed by the dentist, from the plaster composition of the model material, and the like.

This results in an enormous reduction in work load for the dentist and for the laboratory. The occlusal grinding in of the castings for fitting to the patient can practically completely be eliminated. The patient is thereby substantially less inconvenienced and less time is required of them. The targeted high fitting precision results in minimal cement gaps, so that the danger of the production of secondary cavities by erosion of the cement is practically eliminated. The invention further provides the advantage, that even in the new beginning of a collaboration between a dentist and a dental laboratory immediately even with the first patent an exact form fitting production of the casting is made possible, without first requiring working on the patient and inconveniencing the patient with testing. If the dentist or the dental laboratory uses new materials or changes individual components, then with the help of the process according to the invention a quick and problem free conversion is made possible.

BRIEF DESCRIPTION OF THE DRAWINGS

An illustrated embodiment of the test shape employed for the process according to the invention is shown in the drawing.

Therein is shown
FIG. 1 a top view of the test shape and
FIG. 2 a side view of the test shape.

DETAILED DESCRIPTION OF THE INVENTION

Figure 1:
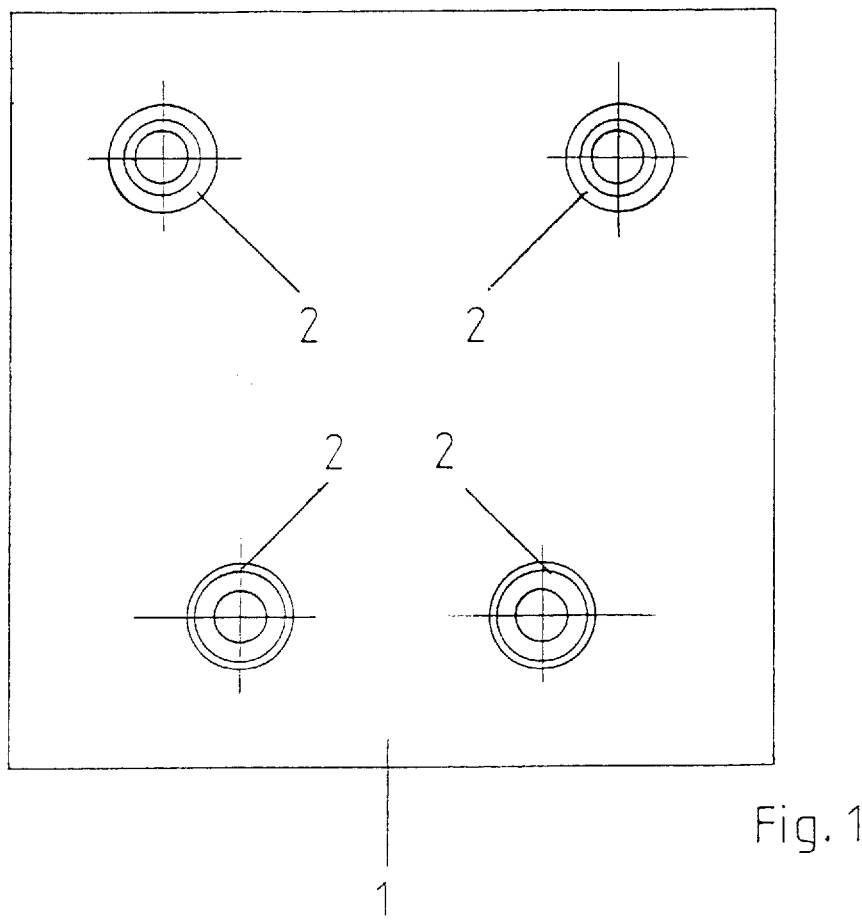
Figure 2:
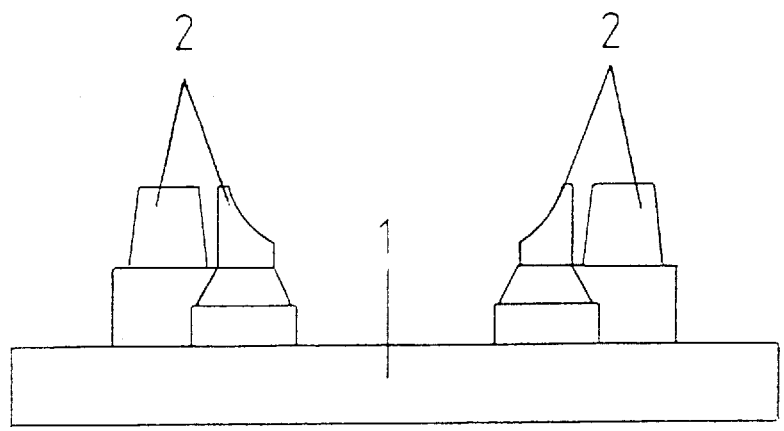

The test shape is comprised of a steel plate 1, upon which phantom teeth stumps 2 are formed unitarily with the steel plate 1. In the illustrated embodiment four phantom tooth stumps 2 are provided. The phantom tooth stumps 2 are ground or polished according to the preparation of the tooth stumps in a patient and exhibit a conicity of for example 6°.

What is claimed is:

1. A process for production of form fitting dental castings, said process comprising:
   (a) taking an imprint of a pre-formed test body with phantom tooth stump(s) with an imprint taking material to form a negative of the phantom tooth stump(s),
   (b) casting the imprint of the phantom tooth stump(s) with a modeling material to produce a test model of the phantom tooth stump(s),
   (c) forming a test model of a dental test casting over the test model of the phantom tooth stump(s),
   (d) using a casting matrix to form a mold around the test model of the dental test casting,
   (e) casting, in the mold, the dental test casting to be formed,
   (f) fitting the dental test casting to the pre-formed test body with phantom tooth stump(s),
   (g) as necessary modifying the casting matrix and repeating steps (d), (e), and (f) until an optimal form fitting precision of the dental test casting upon the pre-formed test body with phantom tooth stump(s) is obtained,
   (h) taking an imprint of tooth stump(s) of the patient with an imprint taking material to form a negative,
   (i) casting the patient's imprint with a modeling material to produce a patient tooth stump model,
   (j) forming a model of a desired dental casting over the patient tooth stump model, and
   (k) using the casting matrix obtained in step (g) to provide an optimal form fitting precision of the dental test casting upon the pre-formed test body with phantom tooth stump(s) to form a mold around the model of the dental casting to be formed.

2. A process as in claim 1, wherein the imprint taking material of step (h) is the same material as the imprint taking material of step (a).

3. A process as in claim 2, wherein said imprint taking material is selected from silicones, polyether rubbers and hydrocolloids.

4. A process as in claim 1, wherein said modeling material of steps (b) and (i) are plaster.

5. A process as in claim 1, wherein said models formed in steps (c) and (j) are wax models.

6. A process as in claim 1, wherein the modification of the casting matrix in step (g) is accomplished by changing the ratio of ingredients.

7. A process as in claim 1, wherein said test body is made of metal.

8. A process as in claim 7, wherein said test body is made of steel.

9. A process as in claim 1, wherein said test body is a steel plate (1) with four phantom tooth stumps (2) formed unitarily therewith.

* * * * *